United States Patent [19]

Talboy

[11] Patent Number: 4,611,592
[45] Date of Patent: Sep. 16, 1986

[54] CLAMP FOR HOLDING SURGICAL LINES

[76] Inventor: Glenn E. Talboy, 1414 Warm Springs Ave., Boise, Id. 83701

[21] Appl. No.: 520,715

[22] Filed: Aug. 5, 1983

[51] Int. Cl.⁴ .............................................. A61B 17/28
[52] U.S. Cl. .................................... 128/321; 128/346; 269/257
[58] Field of Search ............... 128/346, 321, 322, 325, 128/DIG. 26; 251/10; 81/425 A, 425 R, 426, 428 R; 269/257, 6; 294/118, 119

[56] References Cited

U.S. PATENT DOCUMENTS

| 859,429 | 7/1907 | Brown . | |
|---|---|---|---|
| 874,253 | 12/1907 | Scott | 81/426 X |
| 2,111,161 | 3/1938 | Wilson | 128/321 |
| 2,468,823 | 5/1949 | Housepian | 128/346 |
| 2,524,337 | 10/1950 | Whittaker | 128/305 |
| 2,565,750 | 8/1951 | Bertino | 81/51 |
| 2,635,238 | 4/1953 | Garland | 1/49.1 |
| 2,977,150 | 3/1961 | Thomas | 294/118 |
| 3,646,939 | 3/1972 | Sklar | 128/321 |
| 3,786,815 | 1/1974 | Ericson | 128/321 |
| 3,807,406 | 4/1974 | Rafferty et al. | 128/318 |
| 3,921,640 | 11/1975 | Freeborn | 128/318 |
| 3,951,138 | 4/1976 | Akopov | 128/17 |
| 4,024,870 | 5/1977 | Sandel | 128/321 |
| 4,120,302 | 10/1978 | Ziegler | 128/322 |

FOREIGN PATENT DOCUMENTS 248155 12/1969 U.S.S.R. .............................. 128/321

Primary Examiner—Michael H. Thaler
Attorney, Agent, or Firm—Laubscher & Laubscher

[57] ABSTRACT

A scissors-type surgical clamp is disclosed, characterized by a recess-defining offset in the clamping portion thereof for holding suction lines, electrical lines, and the like. The clamp includes a pair of resilient, coplanar arm members which are pivotally connected for relative displacement between open and closed positions about a pivot axis arranged normal to the plane defined by the arm members. Each of the arm members includes gripping and clamping portions on opposite sides of the pivot axis. A locking device is provided to lock the gripping portions of the arm members together in a resiliently deformed overcenter condition in which the arm member clamping portions are forced together. The offset is provided in the clamping portion of one of the arm members and extends in a direction normal to the plane of the arm members to define at least one recess having a depth greater than the thickness of the clamping portion of the other arm member. When a suction line or the like is arranged in the recess and when the gripping portions of the clamp are locked together to secure the clamping portions to a surgical curtain or the like, the suction line is retained in the recess by the offset of the one arm member and by the clamping portion of the other arm member.

4 Claims, 6 Drawing Figures

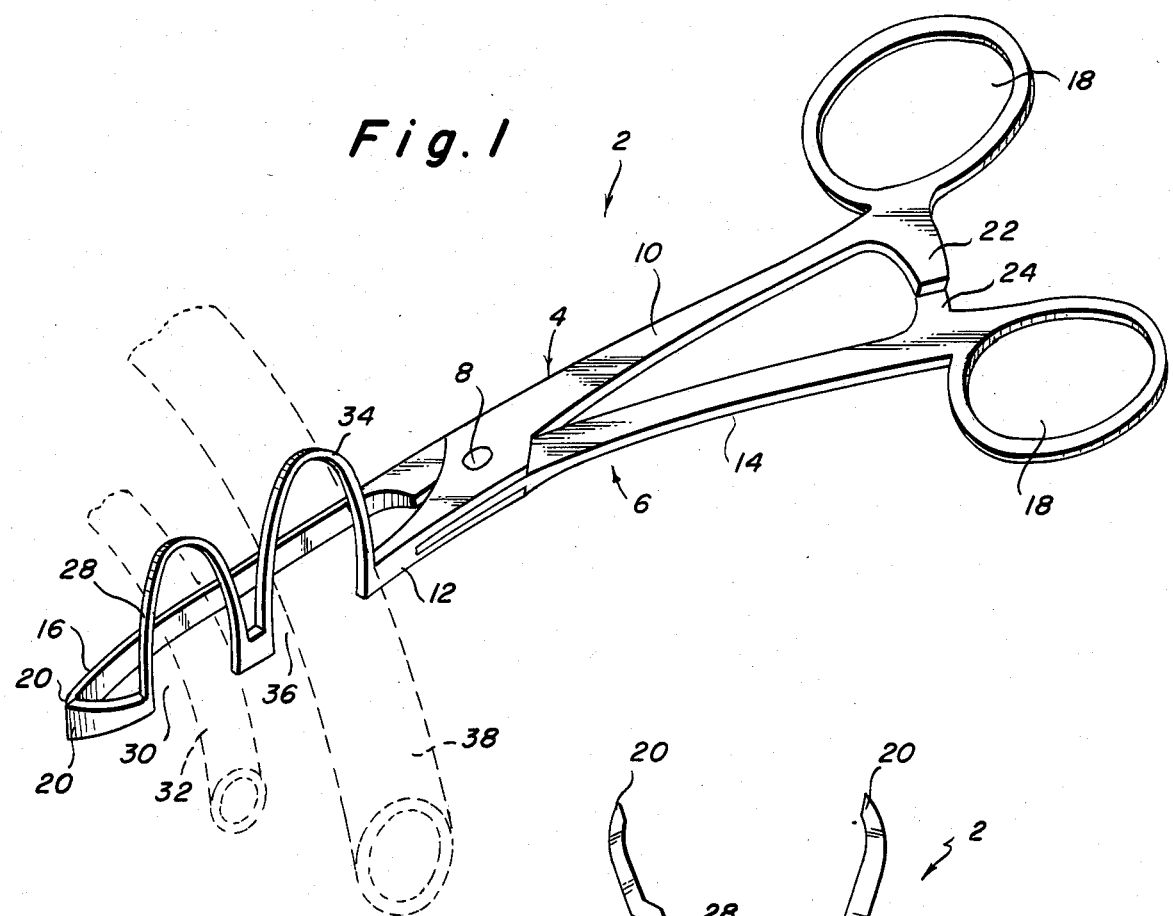
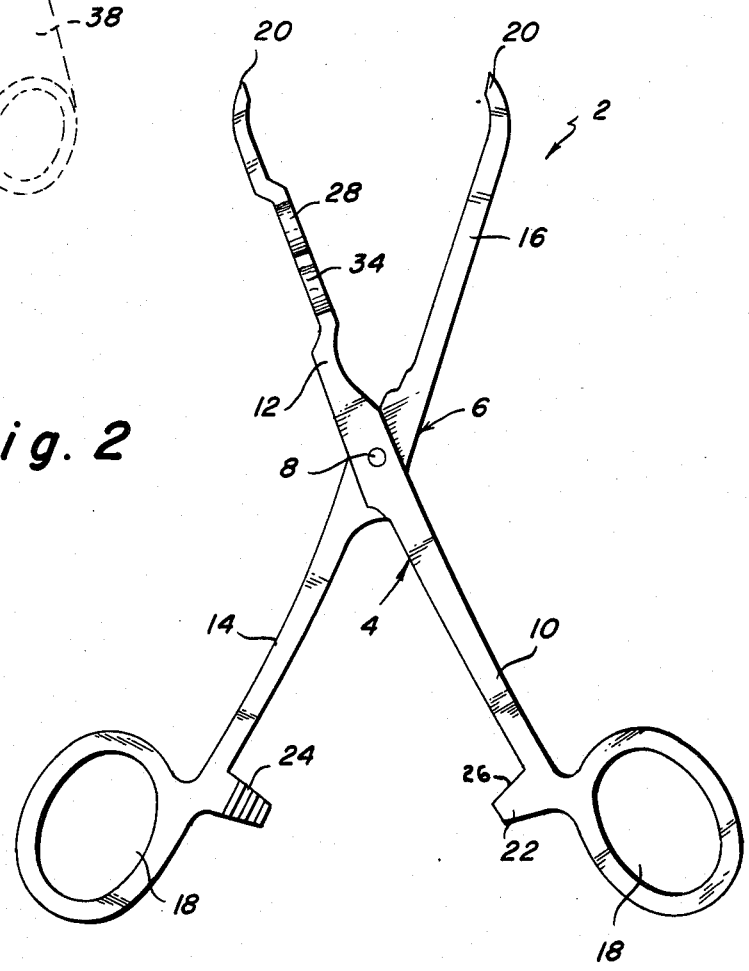

Fig. 3a
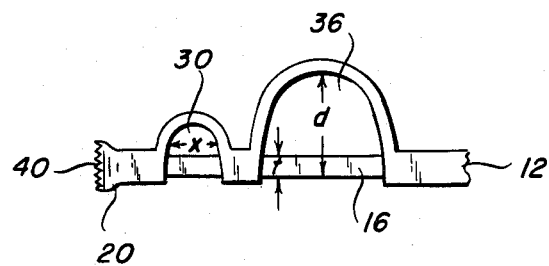
Fig. 3b
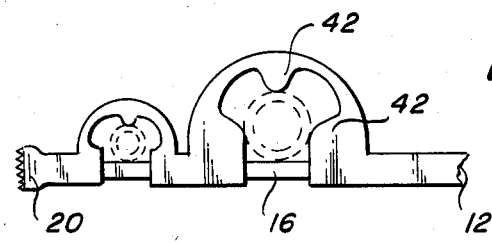
Fig. 3c
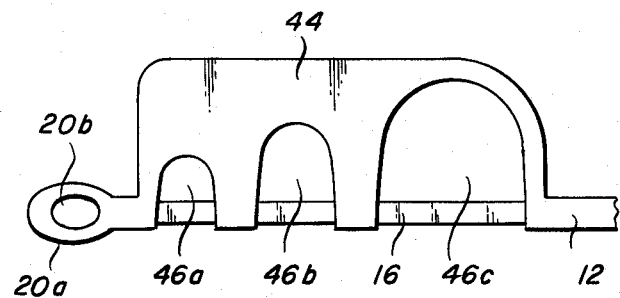
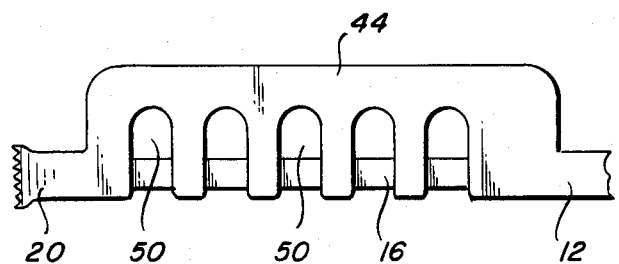
Fig. 3d

CLAMP FOR HOLDING SURGICAL LINES

BACKGROUND OF THE INVENTION

During the performance of a surgical operation, a number of surgical lines are present to assist the surgeon. Generally, a suction line is provided for withdrawing fluids and debris from the surgical site together with electrical lines for delivering electrical current to cauteries, lamps and the like. Gas lines may also be provided. Normally, the surgical lines are either held by a nurse or other surgical assistant, or they are allowed to dangle on the floor of the operating room so that they do not hinder the surgeon.

The present invention relates to a clamp for holding surgical lines such as suction lines, electrical lines, and the like to prevent them from falling to the unsterile floor of the operating room(where they are likely to be stepped on or tripped over )without the aid of a nurse or other surgical assistant.

BRIEF DESCRIPTION OF THE PRIOR ART

Surgical clamps for gripping towels, sterile articles and the like are well-known in the patented prior art as evidenced by the patents to Wilson U.S. Pat. No. 2,111,161, Thomas U.S. Pat. No. 2,977,150, Sklar U.S. Pat. No. 3,646,939, and Freeborn U.S. Pat. No. 3,921,640. While the prior clamps normally operate quite satisfactorily and are still in use today, they have the inherent drawback of not being able to retain surgical lines unless the lines are tied about the clamp.

Accordingly, various clamps were developed for retaining surgical lines as shown by the patents to Housepian U.S. Pat. No. 2,468,823 and Ericson U.S. Pat. No. 3,786,815. A significant drawback of these retaining clamps is that they do not retain the lines flush against the surgical curtain to which the clamps are secured. In the Housepian clamp, for example, the lines which are to be retained extend from the clamp parallel to the pivot axis thereof. Thus when the clamp is arranged flush against the surgical curtain, the line extends outwardly therefrom. Conversely, when the line is arranged against the curtain, the handle of the clamp extends outwardly therefrom. Such an arrangement results in a protruding obstruction which hinders the work of the surgeon and the surgical assistants. A further drawback of the prior devices is that, in order to secure the clamp to the surgical curtain, the line holder pinches or constricts the line. In the case of a suction line, where the line is constricted, the amount of suction will be significantly reduced. Constriction of electrical lines will damage the insulation layer and eventually result in a short in the line or an electrical shock to the surgeon.

The present invention was developed to overcome these and other drawbacks of the prior devices by providing a surgical clamp for holding surgical lines and the like wherein the clamp and lines are arranged flush against the surgical curtain to which the clamp is secured, and further wherein pinching of the lines is avoided.

SUMMARY OF THE INVENTION

Accordingly, it is a primary object of the present invention to provide a surgical clamp for holding surgical lines including a pair of generally coplanar resilient arm members pivotally connected together intermediate their ends. The arm members are pivotally displaced between open and closed conditions relative to each other about a pivot axis normal to the plane defined by the arm members and include corresponding clamping and gripping portions on opposite sides of the pivot axis, respectively. A locking device is provided on the arm members for locking the gripping portions together in a resiliently deformed overcenter condition in which the clamping portions are tightly forced together. The clamping portion of one of the arm members includes an offset portion that is offset in a direction normal to the plane of the arm members. The offset portion defines at least one recess having a depth greater than the thickness of the clamping portion of the other arm member. When a surgical line is arranged in the recess and the gripping portions are locked together with a surgical curtain arranged between the clamping portions, the surgical line is retained within the recess adjacent the surgical curtain by the offset portion of the one arm member and by the clamping portion of the other arm member.

According to a further object of the invention, the recess has a generally U-shaped configuration and an inner diameter corresponding with the outer diameter of the surgical line to be retained therein.

According to another object of the invention, the offset portion defines a plurality of recesses, each having an inner diameter corresponding with the outer diameter of one of a plurality of surgical lines, whereby a plurality of lines may simultaneously be retained.

According to yet another object of the invention, the offset portion includes projections which extend into the recesses for retaining the lines.

BRIEF DESCRIPTION OF THE FIGURES

Other objects and advantages of the subject invention will become apparent from a study of the following specification when viewed in the light of the accompanying drawing, in which:

FIG. 1 is a perspective view of the surgical clamp according to the subject invention;

FIG. 2 is a top plan view of the clamp; and

FIGS. 3a–3d are side plan views of alternate embodiments of the offset portions extending from the clamping portion of one of the arms of the clamp.

DETAILED DESCRIPTION

The surgical clamp 2 according to the subject invention is shown in FIGS. 1 and 2. The clamp is formed from a pair of coplanar arm members 4 and 6 which are pivotally connected in scissors-like fashion by a pin 8 about a pivot axis which extends normal to the plane defined by the arm members. The arm members both include corresponding gripping and clamping portions on opposite sides of the pivot pin 8. More particularly the first arm member 4 includes a gripping portion 10 and a clamping portion 12, while the second arm member 6 includes a gripping portion 14 and a clamping portion 16. Each gripping portion includes an opening 18 adapted to receive the finger of the surgeon or other user of the clamp, and each clamping portion includes at its remote end a clamping tip 20.

Owing to the pivotal connection, the arm members are operable for relative pivotal displacement between an open condition as shown in FIG. 2 and a closed position wherein the gripping portions of the clamp are brought together. As is evident from FIG. 2, the arm members 4 and 6 are slightly bowed inwardly and thus have a convex, as opposed to linear, configuration. Moreover, each arm member is slightly resilient. Therefore, when the gripping portions 10 and 14 are brought closer together beyond the closed condition, they are resiliently deformed into an overcenter condition in which the clamping portions 12 and 16 of the clamp, and thus the clamping tips 20, are tightly forced together as shown in FIG. 1.

The gripping portion 10 of the first arm member 4 includes an inwardly extending first locking device 22 adjacent the opening 18 and the gripping portion 14 of the second arm member 6 includes a corresponding inwardly extending locking device 24. The locking devices are arranged in overlapping relation when the gripping portions are brought into the overcenter condition. The opposing surfaces 26 of the locking devices are serrated and adapted for interlocking to lock the gripping portions in the overcenter condition, whereby the clamping portions are forced together. Preferably, the serrations of the opposed surfaces are arranged at an angle to assist in retaining the gripping portions of the clamp in the locked condition. The gripping portions may be unlocked by disengaging the opposed serrated edges of the locking devices.

The characterizing feature of the present invention is the provision of an offset portion 28 extending from the clamping portion of one of the arm members in a direction normal to the plane of the arm members. In the drawing, the offset portion 28 is shown as extending from the clamping portion 12 of the first arm member 4. It will be appreciated to those skilled in the art that the offset could alternatively be arranged in the clamping portion 16 of the second arm member. The offset portion defines a recess 30 which is adapted to receive a surgical line 32 such as an electrical line. A second offset portion 34 may also be provided to define a second recess 36 adapted to receive a second surgical line 38 such as a suction line.

FIGS. 3a-3d illustrate various alternate embodiments of the offset portion 28. The embodiment shown in FIG. 3a corresponds with that shown in FIG. 1. The recesses 30 and 36 each have a generally U-shaped configuration and have a depth d greater than the thickness t of the clamping portion 16 of the second arm member 6. The depth of the second recess 36 is greater than the depth of the first recess 30 so that surgical lines of different outer diameters may be retained by the clamp. More particularly, the recesses are designed to have an inner diameter x which corresponds with the outer diamter of the line to be retained.

In operation, the surgical lines to be retained are arranged in the recesses of the appropriate size and the clamping tips 20 are arranged on opposite sides of a portion of the surgical curtain which is arranged about the patient. The gripping portions 10 and 14 are locked together in the overcenter condition by the locking devices to force the clamping tips 20 together to clamp the clamp 2 to the surgical curtain. To assist in gripping the curtain, the clamping tips are serrated or knurled at their outer edges as shown by reference numeral 40 shown in FIG. 3a. Since the pivot axis of the arm members is arranged normal to the plane defined by the arm members, the gripping portions 10 and 14 of the arm members 4 and 6, respectively, lie flush against the surgical curtain. More particularly, since the offset portions 28 and 34 extend normal to the plane of the arm members, the surgical lines 32 and 38 extend tranversely through the clamp and are also arranged flush against the surgical curtain. With this construction, neither the clamp nor the surgical lines extend outwardly from the curtain to form an obstruction which would hinder the performance of the surgeon.

As shown in the drawing, the surgical lines are retained in the recess by the offset portions 28 and 34 of the clamping portion 12 of the first arm member and by the clamping portion 16 of the second arm member 6. Since the inner diameters of the recesses are adapted to correspond with the outer diameters of the lines, the lines are retained within the recesses without being constricted or pinched. Moreover, the lines may be freely displaced laterally through the recesses in accordance with the requirements of the surgeon in the performance of the surgical operation.

To assist in retaining the lines within the recesses, each offset portion may contain one or more inwardly extending projections 42 as shown in FIG. 3b. The projections are adapted to retain the lines at spaced areas about the circumference thereof.

The preferred construction of the offset portion is shown in FIGS. 3c and 3d. There, a single offset portion 44 is provided which contains a plurality of recesses 46 for receiving a plurality of lines. In the embodiment of FIG. 3c, three recesses are provided, and the inner diameters of successive recesses increase in the direction of the pivot axis. Thus, for example, the first recess 46a is adapted to retain an electrical surgical line, the second recess 46b is adapted to retain a gas supply line or the like, and the third recess 46c is adapted to retain a suction line.

FIG. 3c also illustrates an alternative embodiment of the clamping tips 20a wherein the tips are ovaloid in configuration and contain a central opening 20b.

In the embodiment of FIG. 3d, the offset portion 48 defines a plurality of recesses 50 which are generally of the same size and are adapted to receive surgical lines such as those required for arthroscopy.

The provision of a single block-shaped offset portion containing one or more recesses as shown in FIGS. 3c and 3d is characterized by increased structural strength as opposed to the offset portions illustrated in FIGS. 3a and 3b. The increased strength is particularly important when the clamp is molded from a nylon/synthetic plastic material having the appropriate degree of resiliency.

The clamp may also be molded from stainless steel material which is suitable for use with all configuration of the offset portion.

Since each embodiment of the clamp differs only in the type of offset portion provided on the clamping portion of the second arm member, a universal clamp mold may be provided to form the clamp, with interchangeable molds being provided for the offset containing clamping portion of the second arm member, whereby the molded clamps will be formed with the desired configuration of the offset portion defining the recesses of the desired number and size.

It will be appreciated by those skilled in the art that configurations of the offset portion other than those illustated in the drawing may be provided to retain the lines required for other surgical procedures including the implantation of pacemakers and the like.

While in accordance with the provisions of the Patent Statutes the preferred forms and embodiments of the subject invention have been illustrated and described, it will be apparent to those skilled in the art that various changes and modifications may be made without deviating from the inventive concepts set forth above.

What is claimed is:

1. A scissors-type surgical clamping device for holding surgical lines such as suction lines, electrical lines, and the like, comprising
    (a) a pair of generally coplanar resilient arm members pivotally connected together intermediate their ends for relative pivotal displacement between open and closed conditions relative to each other about an axis normal to the plane defined by said arm members, said arm members including corresponding clamping and gripping portions on opposite sides of said pivot axis, respectively; and
    (b) locking means for locking together said gripping portions in a resiliently deformed overcenter condition in which the clamping portions are tightly forced together;
    (c) the clamping portion of one of said arm members including an offset portion that is offset in a direction normal to the plane of said arm members, said offset portion including a plurality of generally U-shaped recesses the depths of which are greater than the thickness of the clamping portion of the other arm member, the inner diameters of successive recesses increasing in the direction toward said pivot axis and corresponding with the outer diameters of the lines to be retaind therein, respectively, whereby when a surgical line is arranged in each recess and said gripping portions are locked together with a surgical curtain arranged between said clamping portions, the surgical line is retained and longitudinally displaceable within the recess adjacent the surgical curtain by said offset portion of said one arm member and by the clamping portion of said other arm member.

2. Apparatus as defined in claim 1, wherein the inner surface of said offset portion contains at least one projection member extending into said recesses, respectively, for retaining the lines.

3. Apparatus as defined in claim 2, wherein said arm members and said locking means are formed of stainless steel.

4. Apparatus as defined in claim 2, wherein said arm members and said locking means are formed of nylon synthetic plastic material.

* * * * *